Figure 1:
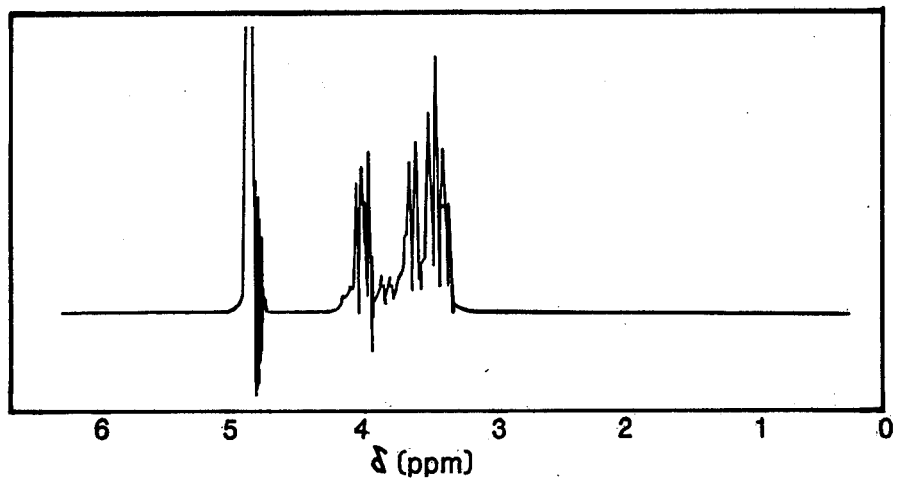

United States Patent

Ishii et al.

[11] Patent Number: 4,481,150
[45] Date of Patent: Nov. 6, 1984

[54] PROCESS FOR PREPARING HYDROXYALKYLAMINOSULFONIC ACIDS

[75] Inventors: Keizou Ishii; Ryuzo Mizuguchi; Shinichi Ishikura; Tamotsu Yoshioka, all of Ikedanaka, Japan

[73] Assignee: Nippon Paint Co., Ltd., Osaka, Japan

[21] Appl. No.: 412,977

[22] Filed: Aug. 27, 1982

Related U.S. Application Data

[63] Continuation-in-part of Ser. No. 214,434, Dec. 8, 1980, abandoned.

[51] Int. Cl.³ ............................................ C07C 143/02
[52] U.S. Cl. .................................................. 260/513 N
[58] Field of Search ..................................... 260/513 N

[56] References Cited

U.S. PATENT DOCUMENTS 2,040,626  5/1936  Nicodemus et al. ........... 260/513 N
3,190,907  6/1965  Distler et al. ................... 260/513 N Primary Examiner—Alan Siegel
Attorney, Agent, or Firm—Wenderoth, Lind & Ponack

[57] ABSTRACT

A process for preparing hydroxyalkylaminosulfonic acids which comprises reacting a hydroxyalkylamine of the formula:

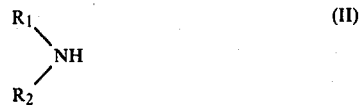

wherein $R_1$ is a $C_1$-$C_{20}$ hydroxyalkyl group optionally containing —O— or —COO— in the alkyl chain, and $R_2$ is a hydrogen atom, a $C_1$-$C_{20}$ hydroxyalkyl group optionally containing —O— or —COO— in the alkyl chain, or a lower alkyl group, with an alkali metal salt of an α,β-unsaturated sulfonic acid of the formula:

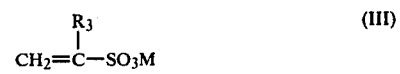

wherein $R_3$ is a hydrogen atom or a methyl group and M is an alkali metal, followed by elimination of the alkali metal to give a hydroxyalkylaminosulfonic acid of the formula:

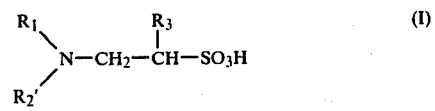

wherein $R_1$ and $R_3$ are each as defined above and $R_2'$ is a hydrogen atom, a $C_1$-$C_{20}$ hydroxyalkyl group optionally containing —O— or —COO— in the alkyl chain, a lower alkyl group or a group of the formula:

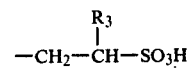

wherein $R_3$ is as defined above.

4 Claims, 6 Drawing Figures

PROCESS FOR PREPARING HYDROXYALKYLAMINOSULFONIC ACIDS

This is a continuation-in-part application of our copending application Ser. No. 214,434 filed Dec. 8, 1980, now abandoned.

The present invention relates to a process for preparing hydroxyalkylaminosulfonic acids.

Hydroxyalkylaminosulfonic acids are biochemically useful substances and are employed as buffer agents. Further, they are used as penetrating agents, emulsion stabilizers, antistatic agents, pigment dispersing agents, etc., because of their surface activity. Furthermore, they are used as reagents for introducing an aminosulfonic acid residue into polymers and oligomers by utilization of the reactivity of the hydroxyl group therein.

For production of hydroxyalkylaminosulfonic acids, there are known various methods, among which typical ones are as follows: (1) a method wherein a hydroxyalkylamine is reacted with a metal salt of halogenated alkylsulfonic acid, followed by elimination of the metal halide (Croatica Chemica Acta, 45, 523–524 (1973)); (2) a method wherein a 1,2-epoxyalkane is reacted with a metal salt of aminoalkylsulfonic acid, followed by elimination of the metal (Japanese Patent Publication (unexamined) No. 95969/1972); (3) a method wherein a hydroxyalkylamine is reacted with a vinylsulfonic ester, followed by hydrolysis (Belgian Pat. No. 617,781), etc. In the method (1), however, repeated performance of recrystallization is necessary for removal of the metal halide, and as the result, the yield of the objective substance is decreased. The method (2) can be applied only to the production of compounds having a hydroxyl group at the β-position. Further, a side reaction proceeds with production of diols so that the yield of the objective substance is lowered. In the method (3), the starting ester compound is unstable and hardly available on the market. In addition, some side reactions proceed with ease, and the yield of the objective substance is naturally lowered.

As the result of an extensive study, it has now been found that the reaction of a hydroxyalkylamine with an alkali metal salt of an α,β-unsaturated sulfonic acid, followed by elimination of the alkali metal affords the objective hydroxyalkylaminosulfonic acid in an excellent yield without the drawbacks of the conventional methods as discussed above.

According to the present invention, there is provided a process for preparing hydroxyalkylaminosulfonic acids which comprises reacting a hydroxyalkylamine of the formula:

wherein $R_1$ is a $C_1$–$C_{20}$ hydroxyalkyl group optionally containing —O— or —COO— in the alkyl chain, and $R_2$ is a hydrogen atom, a $C_1$–$C_{20}$ hydroxyalkyl group optionally containing —O— or —COO— in the alkyl chain, or a lower alkyl group, with an alkali metal salt of an α,β-unsaturated sulfonic acid of the formula:

wherein $R_3$ is a hydrogen atom or a methyl group and M is an alkali metal, followed by elimination of the alkali metal to give a hydroxyalkylaminosulfonic acid of the formula:

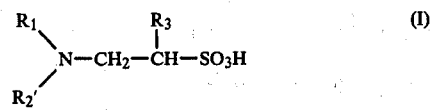

wherein $R_1$ and $R_3$ are each as defined above and $R_2'$ is a hydrogen atom, a $C_1$–$C_{20}$ hydroxyalkyl group optionally containing —O— or —COO— in the alkyl chain, a lower alkyl group or a group of the formula:

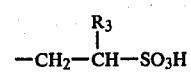

wherein $R_3$ is as defined above.

Examples of the hydroxyalkylamine compound (II) to be used in the process of the invention are 2-aminoethanol, 2-methylaminoethanol, 2-ethylaminoethanol, 2-propylaminoethanol, 2-butylaminoethanol, 2-pentylaminoethanol, 2-aminopropanol-(1), 2-methylaminopropanol-(1), 2-ethylaminopropanol-(1), 2-propylaminopropanol-(1), 2-butylaminopropanol-(1), 2-pentylaminoethanol, 3-aminopropanol-(1), 3-methylaminopropanol-(1), 3-ethylaminopropanol-(1), 3-propylaminopropanol-(1), 3-butylaminopropanol-(1), 3-pentylaminopropanol-(1), 1-aminopropanol-(2), 1-methylaminopropanol-(2), 1-ethylaminopropanol-(2), 2-aminobutanol-(1), 2-methylaminobutanol-(1), 2-ethylaminobutanol-(1), 3-aminobutanol-(1), 3-methylaminobutanol-(1), 3-ethylaminobutanol-(1), 4-aminobutanol-(1), 1-aminobutanol-(2), 3-aminobutanol-(2), 2-amino-2-methylpropanol, 2-aminopentanol-(1), 1-aminopentanol-(2), 2-amino-2-methylbutanol-(1), 1-amino-2-methylbutanol-(2), 3-amino-2-methylbutanol-(2), 2-amino-2-methylbutanol-(3), 2-amino-2-methylbutanol-(4), 3-amino-2-methylbutanol-(4), 3-amino-2,2-dimethylpropanol-(1), 2-aminohexanol-(1), 3-aminohexanol-(2), 5-amino-2-methylpentanol-(4), 4-amino-2-methylpentanol-(5), 2-methyl-2-aminomethylbutanol-(1), 3-amino-2,3-dimethylbutanol-(1), 2-aminoheptanol-(3), 1-aminoheptanol-(4), 2-aminoheptanol-(4), 3-aminoheptanol-(4), 2-amino-2-methylhexanol-(3), 5-amino-2-methylhexanol-(4), 4-amino-2-methylhexanol-(5), 2-amino-2,4-dimethylpentanol-(1), 1-amino-2,4-dimethylpentanol-(3), 5-aminooctanol-(4), 6-amino-2-methylheptanol-(2), 5-amino-2-methylheptanol-(4), 3-amino-3-methylheptanol-(4), 3-aminomethylheptanol-(4), 4-aminoethylheptanol-(4), 5-amino-3-ethylhexanol-(4), 2-methyl-4-aminomethylhexanol-(3), 2,4-dimethyl-3-aminomethylpentanol-(3), 5-amino-2-methyloctanol-(4), 2-methyl-4-aminomethylheptanol-(3), 3-amino-2,6-dimethylheptanol-(4), 2-aminononanol-(3), 3-aminononanol-(4), 10-aminodecanol-(1), 4-aminomethylnonanol-(5), 5-aminomethylnonanol-(5), 5-amino-2,7-dimethyloctanol-(4), 11-aminoundecanol-(1), 2,8-dimethyl-5-aminomethylnonanol-(5), 13-aminotridecanol-(1), 2-methyl-2-methylaminomethylundecanol-(1), 14-aminotetradecanol-(1), 16-aminohexadecanol-(1), 8-aminomethylpentadecanol-(8), 2-aminooctadecanol-(1), diethanolamine, 1-(2-hydroxyethylamino)propanol-(2), bis(3-hydroxypropyl)amine, bis(2-hydroxypropyl)amine, bis(4-hydroxybutyl)amine, 3-aminopropanediol-(1,2), 2-aminopropanediol-(1,3), 2-aminobutanediol-(1,3), 3-amino-2-methylpropanediol-(1,2), 2-amino-2-methylpropanediol-(1,3), 2-aminopentanediol-(1,5), 2-amino-2-ethylpropanediol-(1,3), 3-aminohexanediol-(1,2), 1-aminohexanediol-(2,3), 2-amino-2-propylpropanediol-(1,3), 2-amino-2-isopropylpropanediol-(1,3), 5-amino-2,8-dimethylnonanediol-(4,6), 2-amino-2-hydroxymethylpropanediol-(1,3), 2-aminomethyl-2-hydroxymethylpentanediol-(1,3), 2-hydroxyethylaminotrishydroxymethylethane, 3-hydroxyethylaminotrishydroxymethylmethane, 5-aminopentanetetrol-(1,2,3,4), etc. These hydroxyalkylamine compounds may be prepared, for example, by reacting an oxysilane compound with ammonia or a primary amine.

As the alkali metal salt of α,β-unsaturated sulfonic acid (III), there may be exemplified alkali metal salts (e.g. sodium salt, potassium salt, lithium salt) of vinylsulfonic acid, isopropenylsulfonic acid, etc.

For carrying out the process of the invention, the hydroxyalkylamine compound (II) is reacted with the alkali metal salt of α,β-unsaturated sulfonic acid (III) in a molar proportion of 2:1–1:2, preferably 1:1–2, in an inert solvent such as water or its mixture with a water-miscible organic solvent (e.g. methanol, ethanol, cellosolve, dimethylformamide, dimethylsulfoxide) at a temperature of 0° to 150° C., preferably of 0° to 90° C., for a time of 10 minutes to 48 hours under normal or elevated pressure, usually while stirring.

The reaction mixture is then subjected to treatment for elimination of the alkali metal (i.e. conversion of the alkali metal salt into the free acid). For instance, the reaction mixture is treated with an ion exchange resin so as to convert the alkali metal salt into the free acid.

The thus produced hydroxyalkylaminosulfonic acid (I) can be isolated by per se conventional separation procedures such as concentration, recrystallization and precipitation with a solvent(s).

As understood from the above, the hydroxyalkylaminosulfonic acid (I) is readily obtainable by simple operations. Advantageously, the yield of the hydroxyalkylaminosulfonic acid (I) is quite excellent.

Practical and presently preferred embodiments of the invention are illustratively shown in the following Examples wherein part(s) and % are by weight.

EXAMPLE 1

In a reaction vessel equipped with a stirrer, deionized water (100 parts) and ethanolamine (61 parts) were charged, and the temperature was elevated up to 80° C. A solution of sodium vinylsulfonate (130 parts) in deionized water (390 parts) was dropwise added thereto under stirring in 30 minutes. After completion of the addition, stirring was continued for further 24 hours. The reaction mixture was then diluted with deionized water to make 2000 parts, and the dilution was passed through a cationic exchange resin ("Amberlite IR-121" manufactured by Organo Inc.). The eluate was concentrated by evaporation under heating, and the residue was recrystallized from ethanol to give white crystals (155 parts). Yield, 92%.

By analysis of NMR and IR spectra, the thus obtained substance was proved to have the following structure:

HO—CH₂—CH₂—NH—CH₂—CH₂—SO₃H

The NMR chart of this compound (measured in a 5% D₂O solution by MH-100 manufactured by Nippon Denshi Inc.) is shown in FIG. 1 of the accompanying drawing.

EXAMPLE 2

In a reaction vessel, diethanolamine (105 parts) and deionized water (100 parts) were charged, and the temperature was elevated up to 80° C. Sodium vinylsulfonate (130 parts) and deionized water (390 parts) were dropwise added thereto in 30 minutes, and the reaction was continued for 24 hours. The reaction mixture was treated in the same manner as in Example 1 to give white crystals (191 parts).
Yield, 90%.
The thus obtained substance was proved to have the following structure:

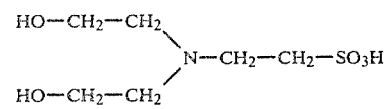

Figure 2:
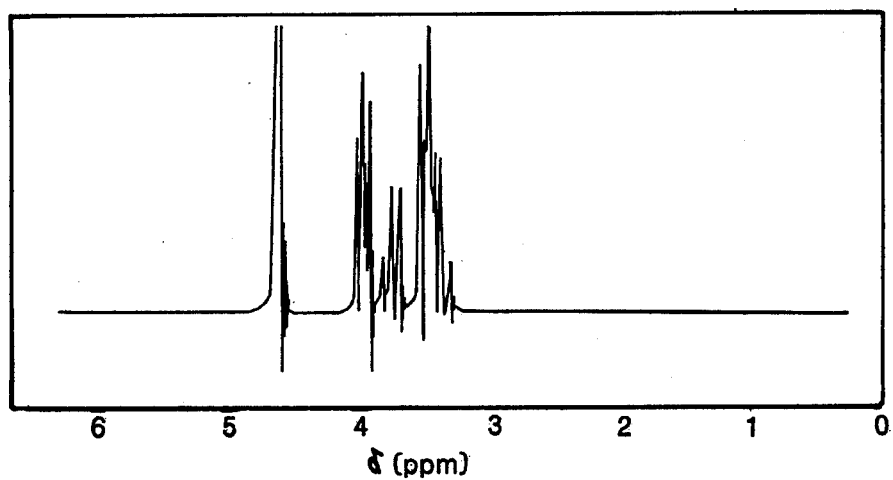

The NMR chart of this compound is shown in FIG. 2.

EXAMPLE 3

In a reaction vessel, sodium vinylsulfonate (260 parts) and deionized water (780 parts) were charged, and after elevation of the temperature up to 80° C., a solution of ethanolamine (61 parts) in deionized wkter (100 parts) was dropwise added thereto in 30 minutes. The reaction was continued for 48 hours. The reaction mixture was treated as in Example 1 to give white crystals (223 parts). Yield, 81%. The thus obtained substance was proved to have the following structure:

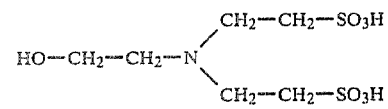

Figure 3:
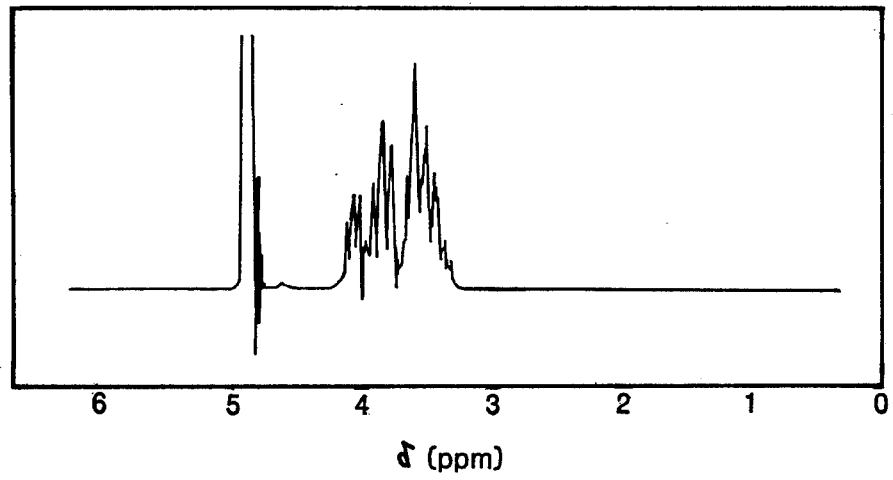

The NMR chart of this compound is shown in FIG. 3.

EXAMPLE 4

In a reaction vessel, 2-methylaminoethanol (75 parts) and deionized water (100 parts) were charged, and after elevation of the temperature up to 80° C., a solution of sodium vinylsulfonate (130 parts) in deionized water (390 parts) was dropwise added thereto in 30 minutes. The reaction was continued for 24 hours. The reaction mixture was treated as in Example 1 to give white crystals (166 parts). Yield, 91%. The thus obtained substance was proved to have the following structure:

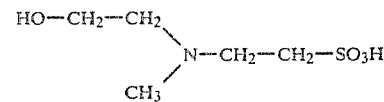

Figure 4:
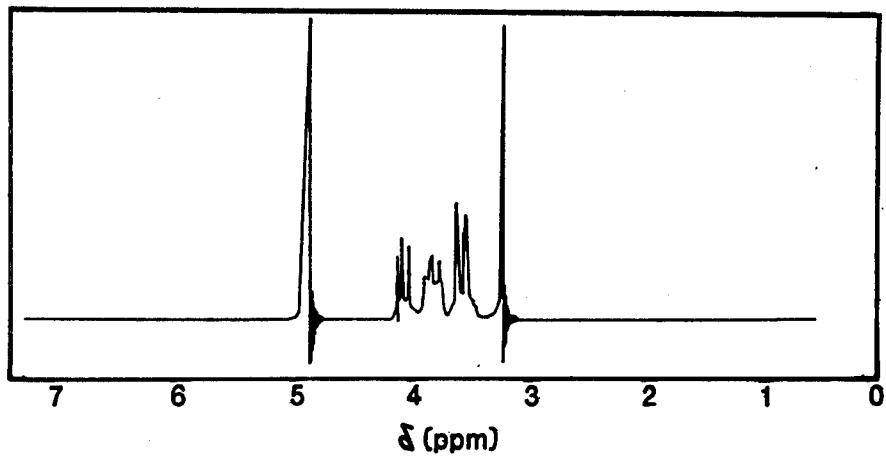

The NMR chart of this compound is shown in FIG. 4.

EXAMPLE 5

In a reaction vessel, tris(hydroxymethyl)aminomethane (121 parts) and deionized water (100 parts) were charged, and after elevation of the temperature up to 90° C., a solution of sodium vinylsulfonate (130 parts) in deionized water (390 parts) was dropwise added thereto in 30 minutes. The reaction was continued for 48 hours. The reaction mixture was treated as in Example 1 to give white crystals (172 parts). Yield, 75%. The thus obtained substance was proved to have the following structure:

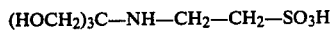
(HOCH$_2$)$_3$C—NH—CH$_2$—CH$_2$—SO$_3$H

Figure 5:
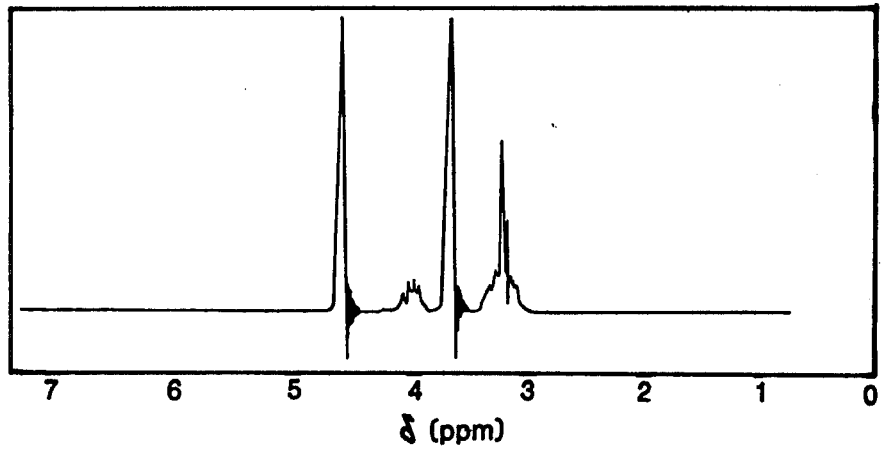

The NMR chart of the sodium salt of this compound is shown in FIG. 5.

EXAMPLE 6

In a reaction vessel, 1-amino-2-propanol (77 parts) and deionized water (100 parts) were charged, and after elevation of the temperature up to 80° C., a solution of sodium vinylsulfonate (130 parts) in deionized water (390 parts) was dropwise added thereto in 30 minutes. The reaction was continued for 48 hours. The reaction mixture was treated as in Example 1 to give white crystals (140 parts). Yield, 77%. The thus obtained substance was proved to have the following structure:

HOCH(CH$_3$)CH$_2$—NH—CH$_2$—CH$_2$—SO$_3$H

Figure 6:
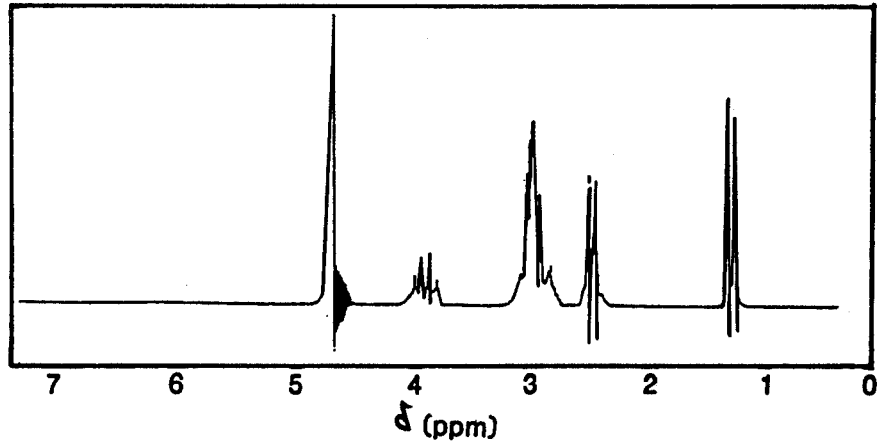

The NMR chart of the sodium salt of this compound is shown in FIG. 6.

EXAMPLE 7

In a reaction vessel, 2-aminooctadecanediol-1,3 (302 parts), ethyl cellosolve (500 parts) and deionized water (310 parts) were charged, and after elevation of the temperature up to 90° C., a solution of sodium vinylsulfonate (130 parts) in deionized water (390 parts) was dropwise added thereto in 1 hour. The reaction was continued for 48 hours. The reaction mixture was concentrated to remove the solvent, and the oil-soluble component was extracted with acetone. The resultant solid component was neutralized with hydrochloric acid to give water-insoluble white powder (360 parts). Yield, 88%. By analysis of the NMR spectrum, the thus obtained substance was proved to have the following structure:

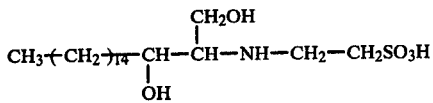

EXAMPLE 8

In a reaction vessel equipped with a stirrer, a 25% methanol solution of ammonia (340 parts) was charged, and butyl glycidyl ether (65 parts) was dropwise added thereto in 2 hours under stirring while maintaining the temperature of 10° C. Stirring was continued for further 6 hours. Then, the temperature was elevated, and unreacted ammonia and methanol were eliminated. Ethyleneglycol monoethyl ether (300 parts) and deionized water (100 parts) were added thereto, and the temperature was elevated up to 70° C. under stirring. A solution of sodium vinylsulfonate (65 parts) in deionized water (200 parts) was dropwise added thereto in 1 hour, and stirring was continued for further 3 hours. The reaction mixture was concentrated by evaporation and extracted with acetone. The resultant solid component was neutralized with hydrochloric acid to give water-insoluble white powder (85 parts). By analysis of the NMR spectrum, the thus obtained substance was proved to have the following structure:

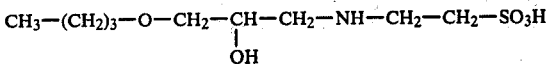
CH$_3$—(CH$_2$)$_3$—O—CH$_2$—CH(OH)—CH$_2$—NH—CH$_2$—CH$_2$—SO$_3$H

EXAMPLE 9

The same procedure as in Example 8 was repeated but using a 40% methanol solution of methylamine (155 parts) in place of the methanol solution of ammonia and a solution of dodecene oxide (92 parts) in ethyleneglycol monoethyl ether (100 parts) in place of butyl glycidyl ether to give white powder (89 parts). By analysis of the NMR spectrum, the thus obtained substance was proved to have the following structure:

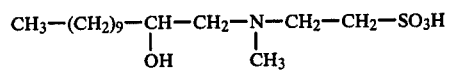

What is claimed is:

1. A process for preparing a hydroxyalkylaminosulfonic acid which comprises
reacting a hydroxyalkylamine of the formula:

(II)

wherein
R$_1$ is C$_1$–C$_{20}$ hydroxyalkyl optionally containing —O— or —COO— in the alkyl chain, and R$_2$ is hydrogen, C$_1$–C$_{20}$ hydroxyalkyl optionally containing —O— or —COO— in the alkyl chain, or lower alkyl, with an alkali metal salt of an α,β-unsaturated sulfonic acid of the formula:

(III)

wherein
R$_3$ is hydrogen or methyl, and M is an alkali metal, in a solvent consisting of water at 0° to 90° C. under normal or elevated pressure, and
eliminating the alkali metal to give the hydroxyalkylaminosulfonic acid, of the formula:

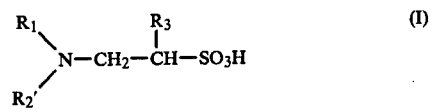
(I)

wherein
R$_1$ and R$_3$ are each as defined above, and R$_2'$ is hydrogen, C$_1$–C$_{20}$ hydroxyalkyl optionally containing —O— or —COO— in the alkyl chain, lower alkyl or a group of the formula:

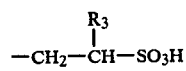

wherein $R_3$ is as defined above.

2. The process according to claim 1, wherein the reaction of (II) with (III) is carried out by treating (II) with (III) in a molar proportion of 2:1–1:2 for a time of 10 minutes to 48 hours while stirring the reaction mixture.

3. The process according to claim 2, wherein the molar proportion of (II) to (III) is 1:1–2.

4. The process according to claim 1, wherein the reaction of (II) with (III) is carried out under normal pressure.

* * * * *